(12) United States Patent
Ikuma et al.

(10) Patent No.: US 12,708,256 B2
(45) Date of Patent: Aug. 18, 2026

(54) PERFUSION DEVICE, PERFUSION METHOD, AND PERFUSION SYSTEM

(71) Applicant: OLYMPUS CORPORATION, Tokyo (JP)

(72) Inventors: Soichi Ikuma, Akishima (JP); Eijiro Sato, Hachioji (JP); Hiroki Kazuno, Koganei (JP); Nagahide Sakai, Kodaira (JP)

(73) Assignee: Olympus Corporation, Tokyo (JP)

( * ) Notice: Subject to any disclaimer, the term of this patent is extended or adjusted under 35 U.S.C. 154(b) by 234 days.

(21) Appl. No.: 18/582,716

(22) Filed: Feb. 21, 2024

(65) Prior Publication Data

US 2024/0188810 A1 Jun. 13, 2024

Related U.S. Application Data

(63) Continuation of application No. PCT/JP2021/031426, filed on Aug. 26, 2021.

(51) Int. Cl.
*A61B 1/015* (2006.01)
*A61B 1/00* (2006.01)

(52) U.S. Cl.
CPC .......... *A61B 1/015* (2013.01); *A61B 1/00091* (2013.01); *A61B 1/00094* (2013.01); *A61B 1/00119* (2013.01)

(58) Field of Classification Search
CPC ............ A61B 1/00068; A61B 1/00091; A61B 1/00094; A61B 1/00119; A61B 1/0014;
(Continued)

(56) References Cited

U.S. PATENT DOCUMENTS

2014/0318582 A1* 10/2014 Mowlai-Ashtiani .......................... A61B 1/00135 134/166 C
2016/0120557 A1 5/2016 Goddard et al.
(Continued)

FOREIGN PATENT DOCUMENTS

JP H11-155807 A 6/1999
JP 2000-279418 A 10/2000
(Continued)

OTHER PUBLICATIONS

International Search Report (with partial translation) and Written Opinion dated Nov. 16, 2021, issued in corresponding International Patent Application No. PCT/JP2021/031426.

*Primary Examiner* — Robert A Lynch
(74) *Attorney, Agent, or Firm* — Morgan, Lewis & Bockius LLP

(57) ABSTRACT

A perfusion device includes an insertion section of an endoscope configured to be insertable inside a subject and including a treatment instrument insertion conduit disposed along a longitudinal axis, and a liquid feeding tube configured to be insertable in the treatment instrument insertion conduit and including an opening at a distal end part, where, in a state where the opening protrudes from a distal end of the treatment instrument insertion conduit, feeding of normal saline can be performed through the opening of the liquid feeding tube and suction of normal saline can be performed through a gap between an outer circumferential surface of the liquid feeding tube and an inner circumferential surface of the treatment instrument insertion conduit, and a flow path for the liquid communicating with the opening of the tube is formed bent along the outer circumferential surface of the tube.

18 Claims, 10 Drawing Sheets

(58) Field of Classification Search
CPC ......... A61B 1/015; A61B 1/018; A61B 17/22; A61B 2217/005; A61B 2217/007; A61M 1/00; A61M 1/77; A61M 1/85; A61M 25/0026; A61M 25/0028; A61M 25/0029; A61M 25/003; A61M 25/0032; A61M 25/0054; A61M 2025/0034; A61M 3/0283
See application file for complete search history.

(56) References Cited

U.S. PATENT DOCUMENTS

| | | | | |
|---|---|---|---|---|
| 2017/0319776 | A1* | 11/2017 | Eisner | A61M 1/772 |
| 2019/0091067 | A1 | 3/2019 | Kraemer | |
| 2021/0085158 | A1 | 3/2021 | Ikuma et al. | |
| 2021/0121188 | A1* | 4/2021 | Yurek | A61M 1/85 |

FOREIGN PATENT DOCUMENTS

| | | | |
|---|---|---|---|
| JP | 2020-534924 | A | 12/2020 |
| WO | 2019/176171 | A1 | 9/2019 |

* cited by examiner 3
44
SALINE BAG
43
PROCESSOR
41
42
LIQUID FEEDING PUMP
SUCTION PUMP
1
31
32
21
P1
P2
P3
12c
12
12b
12a
13
2
11a
11
16
15
14
14a
14b
14c

FIG. 11

SALINE BAG

PROCESSOR

LIQUID FEEDING PUMP

SUCTION PUMP

FIG. 14

LASER DEVICE

SALINE BAG

LIQUID FEEDING PUMP

PROCESSOR

SUCTION PUMP

PERFUSION DEVICE, PERFUSION METHOD, AND PERFUSION SYSTEM

CROSS REFERENCE TO RELATED APPLICATION

This application is a continuation application of PCT/JP2021/031426 filed on Aug. 26, 2021, the entire contents of which are incorporated herein by this reference.

BACKGROUND OF THE INVENTION

1. Field of the Invention

The present invention relates to a perfusion device, a perfusion method, and a perfusion system.

2. Description of the Related Art

There are medical devices for collecting stones such as kidney stones. In the case of collecting a stone such as a kidney stone, a treatment of breaking the stone into smaller fragments and collecting the fragments is performed. For example, U.S. Patent Application Publication No. 2016/0120557 proposes a medical device including a liquid feeding lumen and a suction lumen for providing liquid to a target and for performing suction. Stone fragments obtained by stone dusting are collected through the suction lumen.

When stone dusting takes time, a treatment time for collecting the stone becomes long, and as a result, a great burden is placed on the patient.

Even when not all the stones are broken into tiny particles, if the stones are broken into stone fragments having a certain size or smaller, collection can be performed by using the suction lumen. For example, if the size of stone fragments is reduced to a size that is equal to or smaller than an inner diameter of the suction lumen, the stone fragments can be collected through the suction lumen. If the inner diameter of the suction lumen is increased, stone dusting time may be reduced.

Furthermore, to collect a stone fragment of a relatively large size, a treatment instrument insertion channel of an endoscope may be used as a suction channel, for example.

However, in the case of a kidney stone, if, at the time of stone collection, only suction is performed and liquid is not fed, an organ such as the kidney shrinks, and a field of view of the endoscope is impaired as a result, for example. Accordingly, perfusion is necessary also in the case of using a medical device such as an endoscope for stone collection.

SUMMARY OF THE INVENTION

A perfusion device according to a mode of the present invention includes an insertion appliance configured to be insertable inside a subject, the insertion appliance including a conduit disposed along a longitudinal axis; and a tube configured to be insertable in the conduit, the tube including an opening at a distal end part, where in a state where the opening protrudes from a distal end of the conduit, one of feeding and suction of liquid is allowed to be performed through the opening of the tube, and another of feeding and suction of the liquid is allowed to be performed through a gap between an outer circumferential surface of the tube and an inner circumferential surface of the conduit, and a flow path for the liquid communicating with the opening of the tube is formed bent along the outer circumferential surface of the tube.

A perfusion method according to a mode of the present invention includes inserting a tube including, at a distal end, an opening that is formed bent along an outer circumferential surface, into a conduit of an insertion appliance configured to be inserted into a body; causing the opening of the tube to protrude from a distal end of the conduit; performing one of feeding and suction of liquid from the opening; and performing another of feeding and suction of the liquid through a gap between the outer circumferential surface of the tube and an inner circumferential surface of the conduit.

A perfusion system according to a mode of the present invention includes an insertion appliance configured to be insertable inside a subject, the insertion appliance including a conduit disposed along a longitudinal axis; a tube configured to be insertable in the conduit, the tube including an opening at a distal end part; a liquid supply source configured to supply liquid to the tube; and a fluid control device configured to control a supply flow rate of the liquid by the liquid supply source, where in a state where the opening protrudes from a distal end of the conduit, one of feeding and suction of liquid is allowed to be performed through the opening of the tube, and another of feeding and suction of the liquid is allowed to be performed through a gap between an outer circumferential surface of the tube and an inner circumferential surface of the conduit, and a flow path for the liquid communicating with the opening of the tube is formed bent along the outer circumferential surface of the tube.

BRIEF DESCRIPTION OF THE DRAWINGS

FIG. 11 is a configuration diagram according to a second embodiment, showing a perfusion system including an endoscope and a liquid feeding/suction device;

FIG. 14 is a configuration diagram according to a third embodiment, showing a perfusion system including an endoscope and a liquid feeding/suction device;

DETAILED DESCRIPTION OF THE PREFERRED EMBODIMENTS

Figure 1:
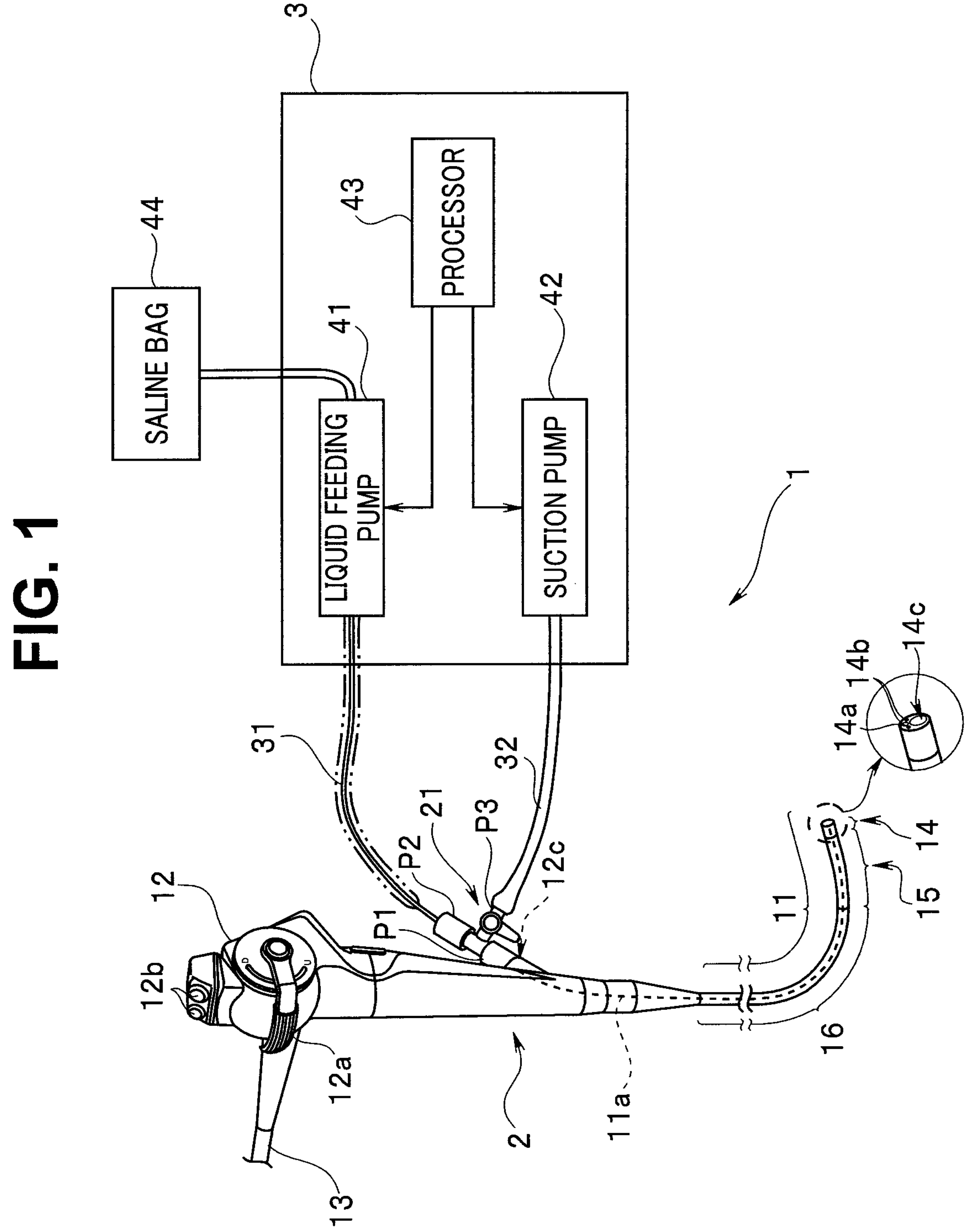
FIG. 1 is a configuration diagram according to a first embodiment, showing a perfusion system including an endoscope and a liquid feeding/suction device.

Note that in each of the drawings used in the following description, the scale of display is different for each component such that each component is large enough to be recognized in the drawing. Accordingly, the present invention is not limited to the modes shown in the drawings with respect to the number of components, the shapes of the components, the proportion of the sizes of the components, and the relative positional relationship of respective components.

First Embodiment (Configuration of Medical System)

FIG. 1 is a configuration diagram of a perfusion system 1 including an endoscope 2 and a liquid feeding/suction device 3. First, a configuration of the endoscope 2 will be described.

The endoscope 2 is an insertion appliance that can be inserted into a subject. The endoscope 2 is a flexible ureteroscope including an insertion section 11, an operation section 12, and a connection cable 13. A connector (not shown) is provided at a proximal end portion of the connection cable 13. The connector can be connected to a video processor (not shown).

The insertion section 11 includes, from a distal end, a distal end portion 14, a bending portion 15, and a flexible tube portion 16, and is configured to be insertable inside a subject. As indicated by a dotted line, the endoscope 2 includes a treatment instrument insertion conduit 11*a* that is disposed along a longitudinal axis of the insertion section 11. An observation window 14*a*, two illumination windows 14*b*, and an opening 14*c* are provided in a distal end surface of the distal end portion 14. The opening 14*c* communicates with the treatment instrument insertion conduit 11*a*.

An image of a subject that is obtained through the observation window 14*a* is displayed on a monitor (not shown) connected to the video processor (not shown).

The operation section 12 of the endoscope 2 is provided with a bending lever 12*a*. A surgeon can bend the bending portion 15 in an up-down direction by operating the bending lever 12*a*. The up-down direction corresponds to an up-down direction in an endoscopic image that is displayed on the monitor (not shown).

A surgeon can insert the insertion section 11 into the subject by operating the bending lever 12*a* of the operation section 12 and bending the bending portion 15 while the surgeon looks at an endoscopic image of inside of the subject that is displayed on the monitor (not shown), and can check presence/absence of a stone in the kidney. Furthermore, the surgeon can perform various functions such as recording of the endoscopic image, by operating operation buttons 12*b* on the operation section 12 that are assigned with various functions.

Furthermore, the operation section 12 of the endoscope 2 is provided with a treatment instrument insertion opening 12*c*. The treatment instrument insertion opening 12*c* communicates with the treatment instrument insertion conduit 11*a* provided inside the insertion section 11. Accordingly, the treatment instrument insertion opening 12*c* communicates with the opening 14*c* through the treatment instrument insertion conduit 11*a*.

Illumination light is emitted from the illumination window 14*b* in the distal end surface of the distal end portion 14. Reflected light of the illumination light from an observation part inside the subject enters the observation window 14*a*. Light entering the observation window 14*a* enters an image pickup surface of an image pickup device 14*a*2 (FIG. 5) that is disposed behind the observation window 14*a*. An image pickup signal from the image pickup device 14*a*2 (FIG. 5) is supplied to the video processor (not shown) through a signal line inserted through the insertion section 11, the operation section 12, and the connection cable 13.

The treatment instrument insertion opening 12*c* is an opening for inserting a treatment instrument, and also allows connection of a T-shaped tube 21.

Figure 2:
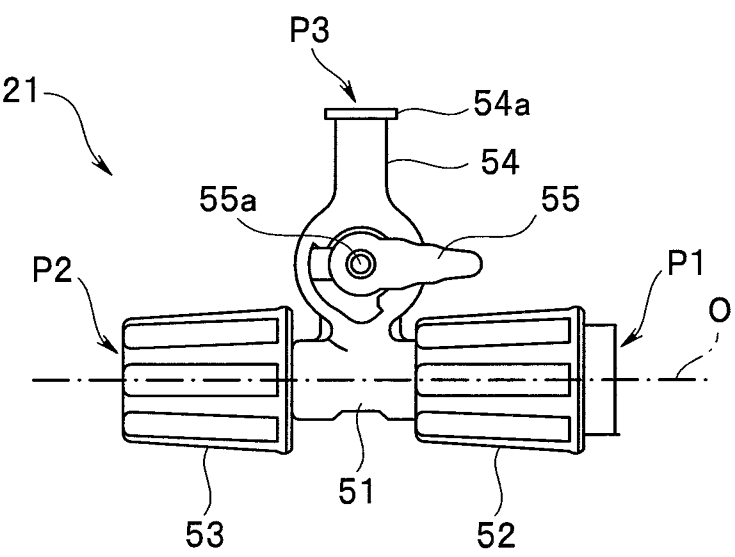
FIG. 2 is a plan view according to the first embodiment, showing a T-shaped tube.

FIG. 2 is a front view of the T-shaped tube 21. The T-shaped tube 21 is made of resin, but metal such as stainless steel may be embedded in a part of the T-shaped tube 21. The T-shaped tube 21 includes three ports.

The T-shaped tube 21 includes a main body 51, a first fixing ring 52 provided on a first port P1, a second fixing ring 53 provided on a second port P2, a liquid feeding pipe sleeve 54 provided on a third port P3, and a cock 55.

The main body 51 is a circular cylindrical member extending along a center axis O. The main body 51 further includes a cylindrical part for the third port P3, the cylindrical part extending in a direction orthogonal to the center axis O. The first port P1 and the second port P2 are located on the center axis O. The third port P3 is located on an axis that is orthogonal to the center axis O.

The first fixing ring 52 is provided at one end of the main body 51, and includes the first port P1. The first fixing ring 52 is an annular member that is fitted with and engages with a pipe sleeve of the treatment instrument insertion opening 12*c* of the endoscope 2, and that fixes the first port P1 of the T-shaped tube 21 to the treatment instrument insertion opening 12*c* in a watertight manner.

Figure 3:
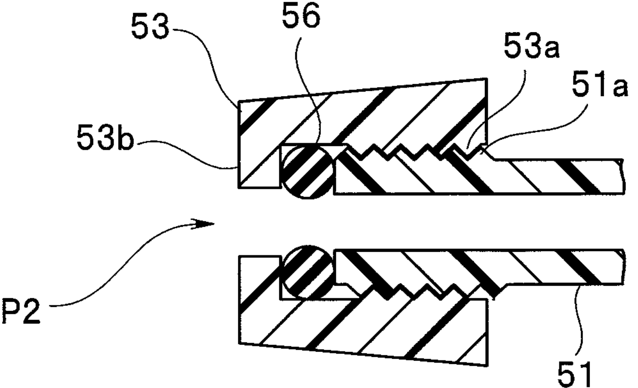
FIG. 3 is a partial cross-sectional view of the T-shaped tube according to the first embodiment, showing a configuration of a second fixing ring.

The second fixing ring 53 is an annular member including the second port P2. The second port P2 is a port for inserting a liquid feeding tube and the like. FIG. 3 is a partial cross-sectional view of the T-shaped tube 21, showing a configuration of the second fixing ring 53. FIG. 3 shows a partial cross-section of the T-shaped tube 21 along the center axis O.

An external thread portion 51*a* is provided on an outer circumferential surface on one end of the main body 51. An internal thread portion 53*a* is provided on an inner circumferential surface on a proximal end side of the second fixing ring 53. The external thread portion 51*a* and the internal thread portion 53*a* are screwed with each other.

An inward flange 53*b* is provided on a distal end side of the second fixing ring 53. An O-shaped ring 56 is disposed inside the second fixing ring 53, such that the O-shaped ring 56 is sandwiched between the inner flange 53*b* and a distal end of the main body 51.

A tube member, such as a liquid feeding tube described later, can be inserted into the T-shaped tube 21 through the port P2 on the inner flange 53*b* side. When the second fixing ring 53 is rotated in a predetermined direction around the center axis O, the O-shaped ring 56 is compressed. The tube member is pressed from an outer side by the compression to be fixed to the T-shaped tube 21 in a watertight and airtight manner.

Furthermore, when the second fixing ring 53 is rotated around the center axis O in a direction opposite to the predetermined direction, compression of the O-shaped ring 56 is released, and the tube member can be moved in the direction of the center axis O relative to the T-shaped tube 21 or can be pulled out.

Referring back to FIG. 2, the liquid feeding pipe sleeve 54 includes an outward flange 54*a* on an end portion. By connecting a luer lock connector fixed at an end portion of the tube member to the liquid feeding pipe sleeve 54, the tube member can be connected and fixed to the T-shaped tube 21.

The cock 55 is a member for controlling a direction of flow of liquid flowing into the T-shaped tube 21. The cock 55 is capable of rotating around a center axis 55*a*. For example, when the cock 55 is at a position shown in FIG. 2, the first port P1 and the second port P2 communicate with each other, but the third port P3 does not communicate with a communication path in the first port P1 and the second port P2. Furthermore, when the cock 55 is rotated around the center axis 55*a* by 90 degrees from the position shown in FIG. 2, the first port P1, the second port P2, and the third port P3 communicate with one another.

The surgeon may change a route of flow of the liquid inside the T-shaped tube 21 by operating a lever of the T-shaped tube 21.

Next, referring back to FIG. 1, a configuration of the liquid feeding/suction device 3 will be described.

The liquid feeding/suction device 3 includes a liquid feeding pump 41, a suction pump 42, and a processor 43. A saline bag 44 containing normal saline is connected to the liquid feeding pump 41. The liquid feeding/suction device 3 includes an operation panel, not shown, and the surgeon may perform a desired function such as start of liquid feeding by operating the operation panel.

The liquid feeding pump 41 and the suction pump 42 are connected to the processor 43. The liquid feeding pump 41 and the suction pump 42 can operate by being controlled by the processor 43. A proximal end of the liquid feeding tube 31 is connected to the liquid feeding pump 41. A proximal end of a liquid suction tube 32 is connected to the suction pump 42.

A distal end portion of the liquid feeding tube 31 is inserted in the treatment instrument insertion conduit 11*a* through the port P2 of the T-shaped tube 21. A perfusion device is configured by the endoscope 2 including the treatment instrument insertion conduit 11*a* and the liquid feeding tube 31 inserted in the treatment instrument insertion conduit 11*a*.

A distal end portion of the liquid suction tube 32 is connected to the port P3 of the T-shaped tube 21.

The port P1 of the T-shaped tube 21 is connected to the treatment instrument insertion opening 12*c* of the endoscope 2.

The processor 43 includes a central processing unit (CPU), a ROM, a RAM, and the like. The CPU implements various functions such as control of driving of the liquid feeding pump 41 and the suction pump 42, by reading out a predetermined control program stored in the ROM and developing the program in the RAM and executing the program that is read according to a command from the surgeon inputted to the operation panel.

When the liquid feeding pump 41 is activated, normal saline from the saline bag 44 is fed into a lumen of the liquid feeding tube 31.

When the suction pump 42 is activated, liquid inside the treatment instrument insertion conduit 11*a* is suctioned through the liquid suction tube 32.

As described above, the surgeon can cause the liquid feeding tube 31 to be inserted into the treatment instrument insertion conduit 11*a* from the treatment instrument insertion opening 12*c* via the T-shaped tube 21, and cause a distal end of the liquid feeding tube 31 to protrude from the opening 14*c*.

Figure 4:
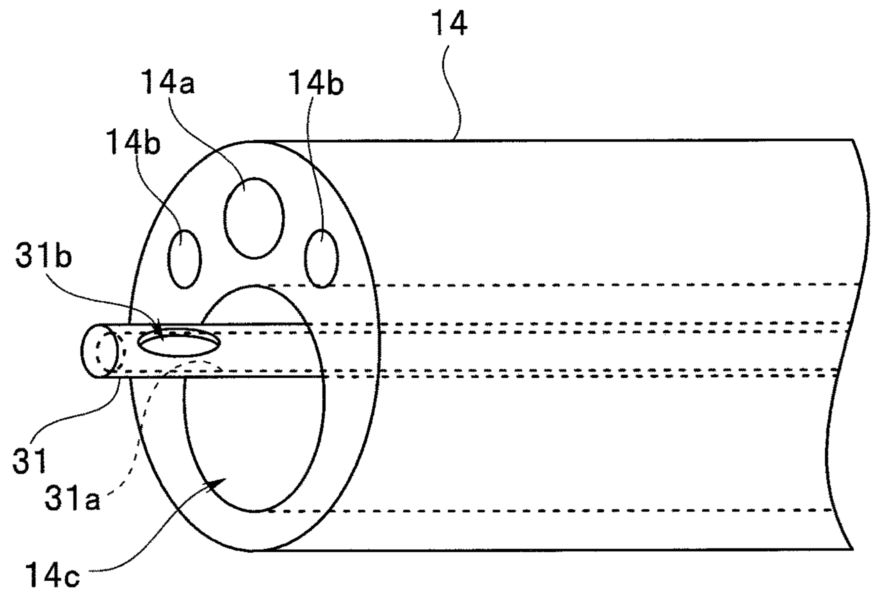
FIG. 4 is a perspective view according to the first embodiment, showing a distal end portion of an insertion section.

FIG. 4 is a perspective view of the distal end portion 14. FIG. 4 shows a state where the liquid feeding tube 31 is inserted in the treatment instrument insertion conduit 11*a* from the treatment instrument insertion opening 12*c* via the T-shaped tube 21, and the distal end of the liquid feeding tube 31 protrudes from the opening 14*c* in the distal end portion 14 of the endoscope 2.

Figure 5:
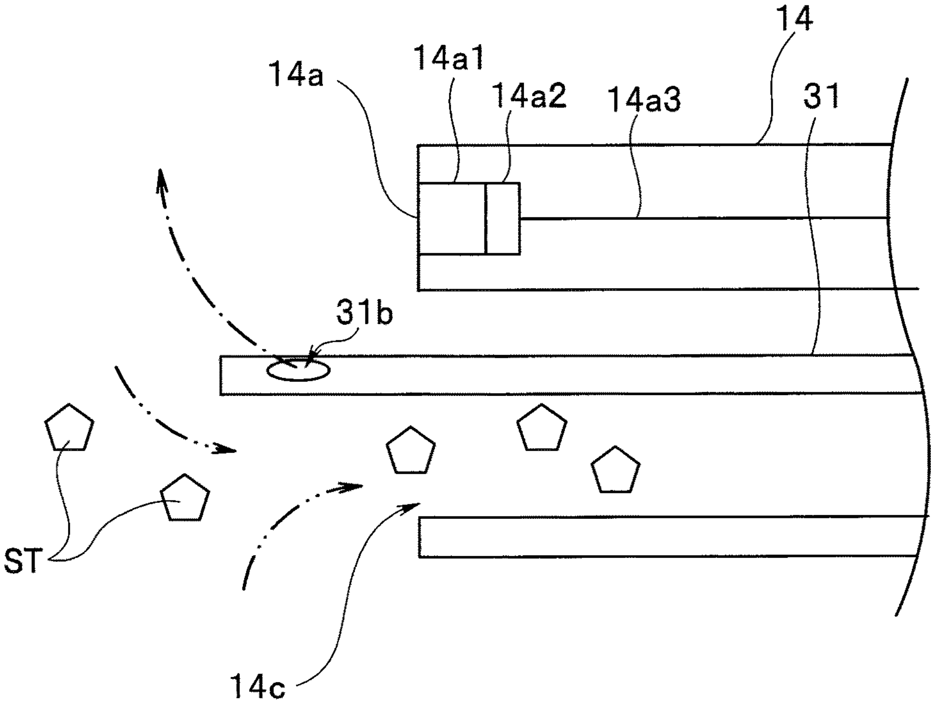
FIG. 5 is a schematic cross-sectional view according to the first embodiment, showing the distal end portion of the insertion section, the cross-sectional view describing collection of stone fragments by liquid feeding and liquid suction at the distal end portion.

As described above, the observation window 14*a* is provided in the distal end surface of the distal end portion 14. An image pickup unit is disposed behind the observation window 14*a*. The image pickup unit includes an observation optical system 14*a*1 and the image pickup device 14*a*2 (FIG. 5). Light from a subject passes through the observation optical system 14*a*1, and is condensed on the image pickup surface of the image pickup device 14*a*2 such as a CMOS image sensor. A subject image formed on the image pickup surface is photoelectrically converted by the image pickup device 14*a*2, and an image pickup signal is generated and outputted to a signal line 14*a*3 (FIG. 5).

A distal end surface of a light guide (not shown), which is an optical fiber bundle for illumination light, is disposed behind each illumination window 14*b*. Light passing through the light guide is emitted as illumination light from each illumination window 14*b*.

Note that, here, the image pickup device 14*a*2 is provided at the distal end portion 14, but an image guide including an optical fiber bundle may be provided behind the observation window 14*a*, and the subject image may be transmitted to an image pickup device of the video processor (not shown) via the image guide.

Here, the illumination light is transmitted by the light guide, but the illumination light may be emitted from each illumination window 14*b* by providing a light emitting device such as an LED at the distal end portion 14.

Next, a configuration of the liquid feeding tube 31 will be described. As shown in FIG. 4, the liquid feeding tube 31 has an outer diameter that allows insertion inside the treatment instrument insertion conduit 11*a*. The outer diameter of the liquid feeding tube 31 is smaller than half of an inner diameter of the opening 14*c* in the distal end portion 14 (that is, an inner diameter of the treatment instrument insertion conduit 11*a*).

The liquid feeding tube 31 includes a lumen 31*a* inside. Liquid, such as normal saline in the present case, can flow inside the lumen 31*a*. A distal end of the liquid feeding tube 31 is closed, but an opening 31*b* is provided in a side surface near the distal end. The opening 31*b* communicates with the lumen 31*a*. In other words, the liquid feeding tube 31 is configured to be insertable in the treatment instrument insertion conduit 11*a*, and includes the opening 31*b* in a distal end part.

An outer diameter of the distal end portion 14 is within a range of 2 to 5 mm, e.g. 3 mm. The inner diameter of the opening 14*c* of the distal end portion 14 is within a range of 0.8 to 2.6 mm, e.g. 1.3 mm. The outer diameter of the liquid feeding tube 31 is within a range of 0.4 to 1.3 mm, e.g. 0.6 mm. An inner diameter of the lumen 31*a* is within a range of 0.3 to 1.1 mm, e.g. 0.4 mm, for example. A longer diameter of the opening 31*b* is within a range of 0.3 to 4 mm, e.g. 1 mm.

As described above, the distal end part of the liquid feeding tube 31 can be inserted from the port P2 of the T-shaped tube 21 to pass through the treatment instrument insertion conduit 11*a* and to protrude from the opening 14*c* in the distal end portion 14.

(Operation)

First, a surgeon attaches the T-shaped tube 21 to a pipe sleeve of the treatment instrument insertion opening 12*c*. In the case of breaking a kidney stone, the surgeon inserts a laser probe (not shown) for breaking a kidney stone from the second port P2 of the T-shaped tube 21. The surgeon can break the stone while the surgeon looks at the endoscopic image, by emitting laser light from the inserted laser probe.

Although not shown, at the time of breaking of the stone, the liquid feeding tube 31 is connected to the port P3 of the T-shaped tube 21, and liquid is fed through the treatment instrument insertion conduit 11*a*.

When the stone is broken into stone fragments of a predetermined size or smaller, the laser probe is removed from the treatment instrument insertion opening 12*c*.

Then, the distal end portion of the liquid suction tube 32 is attached to the third port P3 of the T-shaped tube 21. The distal end part of the liquid feeding tube 31 is inserted into the treatment instrument insertion conduit 11*a* from the second port P2 of the T-shaped tube 21.

The surgeon causes the distal end part of the liquid feeding tube 31 to protrude from the opening 14*c* in the distal end portion 14 while the surgeon looks at the endoscopic image. After checking, by looking at the endoscopic image, that the distal end part of the liquid feeding tube 31 is in a state of protruding from the opening 14*c* in the distal end portion 14, the surgeon rotates the second fixing ring 53 in the predetermined direction around the center axis O and fixes the liquid feeding tube 31 to the T-shaped tube 21.

Then, the surgeon causes the liquid feeding/suction device 3 to operate, and simultaneously performs feeding and suction of normal saline as the liquid. By also taking into account an amount that is discharged through a gap between the endoscope and a urinary duct and the like, the processor 43 drives the liquid feeding pump 41 and the suction pump 42 in such a way that a good balance is achieved between an amount of liquid feeding and an amount of liquid suction.

FIG. 5 is a schematic cross-sectional view of the distal end portion 14 for describing collection of stone fragments by liquid feeding and liquid suction at the distal end portion 14.

Due to liquid feeding, normal saline is fed from the opening 31*b* in the liquid feeding tube 31, as indicated by a dash-dotted line. As indicated by dash-dot-dotted lines, normal saline is suctioned from the opening 14*c*. At the time of suction of normal saline, a stone fragment ST is also suctioned and drawn into the treatment instrument insertion conduit 11*a*. In other words, suction of normal saline is performed through a gap between an outer circumferential surface of the liquid feeding tube 31 and an inner circumferential surface of the treatment instrument insertion conduit 11*a*.

Because the opening 31*b* is in front of the observation window 14*a*, if a position of the opening 31*b* around the center axis of the liquid feeding tube 31 is adjusted by rotating the liquid feeding tube 31 around the center axis of the liquid feeding tube 31, the stone fragment ST in front of the observation window 14*a* is blown away by a liquid current, and a field of view for the endoscopic image may be prevented from being impaired.

The stone fragment ST that is suctioned can pass through a gap between an inner wall of the treatment instrument insertion conduit 11*a* and the outer circumferential surface of the liquid feeding tube 31. In other words, in a state where the opening 31*b* protrudes from a distal end of the treatment instrument insertion conduit 11*a*, liquid is fed from the opening 31*b* in the liquid feeding tube 31, and suction of liquid (normal saline) is performed through the gap between the outer circumferential surface of the liquid feeding tube 31 and the inner circumferential surface of the treatment instrument insertion conduit 11*a*.

With the endoscope of the present embodiment, two tubes, namely, the liquid feeding tube 31 and the liquid suction tube 32, are not provided in parallel with each other inside the insertion section 11, and the number of tubes is reduced from two to one, and only one liquid feeding tube 31 is inserted in one treatment instrument insertion conduit 11*a*. Accordingly, the inner diameter of the treatment instrument insertion conduit 11*a* may be increased within a possible range.

Accordingly, with the perfusion device of the present embodiment, a relatively large stone fragment can be collected, and a stone collecting treatment time can be reduced, and burden on the patient can be reduced.

Next, modifications will be described.

(Modification 1-1)

In the embodiment described above, the outer diameter is the same for the entire liquid feeding tube 31, but in Modification 1-1, a liquid feeding tube 31A includes, at a distal end part, an increased diameter portion with a large outer diameter.

Figure 6:
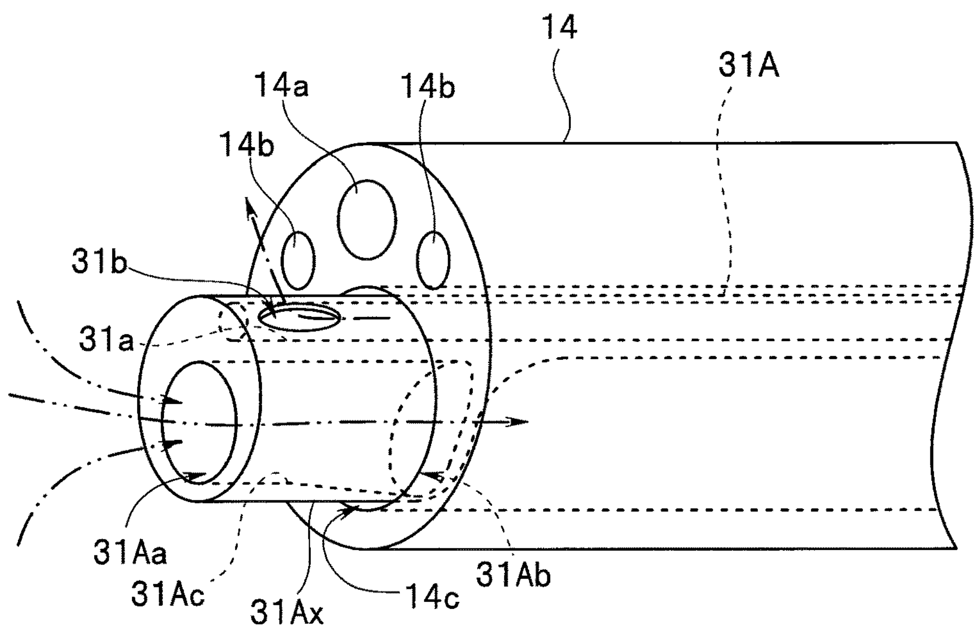
FIG. 6 is a perspective view according to Modification 1-1 of the first embodiment, showing the distal end portion of the insertion section.

FIG. 6 is a perspective view according to Modification 1-1, showing the distal end portion 14. FIG. 6 shows a state where a distal end of the liquid feeding tube 31A protrudes from the opening 14*c* in the distal end portion 14 of the endoscope 2.

As shown in FIG. 6, the liquid feeding tube 31A includes, at a distal end, an increased diameter portion 31Ax. The increased diameter portion 31Ax has a circular cylindrical shape. An outer diameter of the increased diameter portion 31Ax is slightly smaller than the inner diameters of the treatment instrument insertion conduit 11*a* and the opening 14*c*. The increased diameter portion 31Ax includes a distal end opening 31Aa, a proximal end opening 31Ab, and a communication path 31Ac that allows the distal end opening 31Aa and the proximal end opening 31Ab to communicate with each other. The increased diameter portion 31Ax includes the communication path 31Ac having a same inner diameter as an inner diameter of the distal end opening 31Aa. As described later, normal saline that is suctioned can pass through the communication path 31Ac. The inner diameter of the distal end opening 31Aa is smaller than an outer diameter of the increased diameter portion 31Ax.

Note that, as indicated by dotted lines, the communication path 31Ac may be formed in such a way that the inner diameter of the distal end opening 31Aa is smaller than an inner diameter of the proximal end opening 31Ab. In other words, the communication path 31Ac may be formed such that an inner diameter of a proximal end side of the communication path 31Ac is greater than the inner diameter of the distal end opening 31Aa. In other words, the communication path 31Ac becomes thinner or narrower toward the distal end opening 31Aa in the increased diameter portion 31Ax.

The inner diameter of the treatment instrument insertion conduit 11*a* is within a range of 1.0 to 2.6 mm, e.g. 1.8 mm. An outer diameter of the liquid feeding tube 31A is within a range of 0.4 to 1.3 mm, e.g. 0.6 mm, and an inner diameter of the liquid feeding tube 31A is within a range of 0.3 to 1.1 mm, e.g. 0.4 mm. For example, 20 ml of normal saline is fed from the opening 31*b* every minute. The outer diameter of the increased diameter portion 31Ax is within a range of 0.9 to 2.6 mm, e.g. 1.7 mm, for example, and the inner diameter of the distal end opening 31Aa in the increased diameter portion 31Ax is within a range of 0.4 to 2.0 mm, e.g. 1.0 mm.

A length of the increased diameter portion 31Ax in a longitudinal axis direction of the liquid feeding tube 31A is such that a distal end of the increased diameter portion 31Ax is captured in a range of the endoscopic image that is obtained by the observation window 14*a*.

According to the present modification, as indicated by a dash-dotted line, normal saline is fed from the opening 31*b* in a somewhat obliquely forward direction relative to a center axis of the liquid feeding tube 31A. Moreover, suction of normal saline is performed from the distal end opening 31Aa in the increased diameter portion 31Ax. As indicated by dash-dot-dotted lines, normal saline is suctioned via the distal end opening 31Aa. Because only a stone fragment ST of a size that allows passing through the distal end opening 31Aa can be suctioned, blockage of the treatment instrument insertion conduit 11*a* can be reduced or avoided by making a diameter of the distal end opening 31Aa smaller than a suction space (14C-31A) behind the proximal end opening 31Ab. As indicated by the dash-dot-dotted lines, normal saline is suctioned at a position more forward than the distal end surface of the distal end portion 14. Because the position at which the stone fragment ST is suctioned is a position that is more forward than the distal end surface of the distal end portion 14, a stone fragment ST deep in a renal calyx can be suctioned.

(Modification 1-2)

Note that, as Modification 1-2, a distal end part of the increased diameter portion 31Ax may be narrowed to further reduce the inner diameter of the distal end opening 31Aa.

Figure 7:
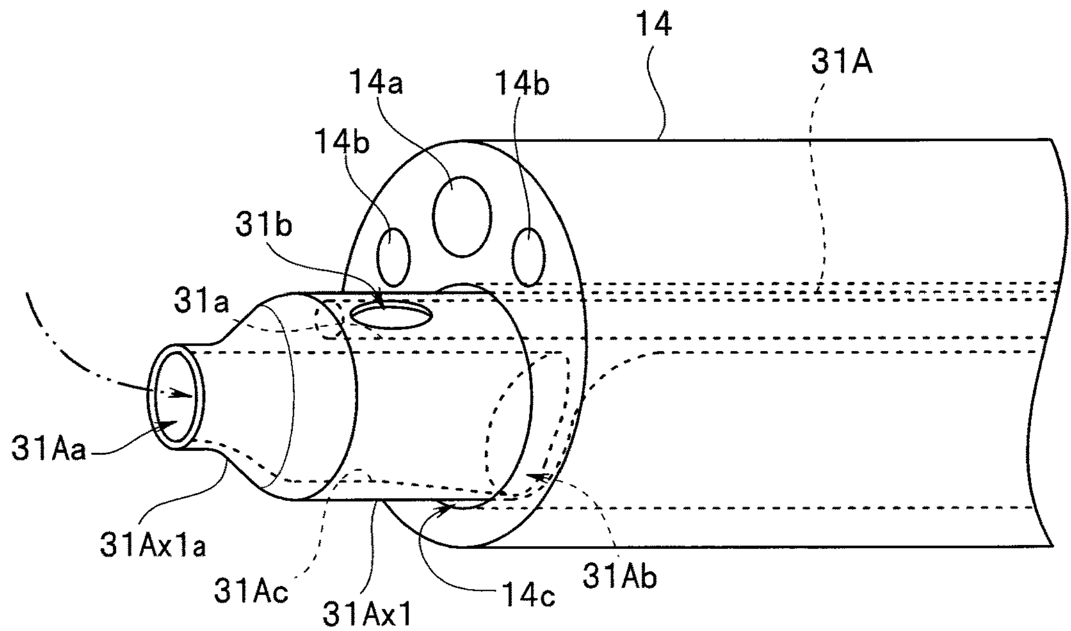
FIG. 7 is a perspective view according to Modification 1-2 of the first embodiment, showing the distal end portion of the insertion section.

FIG. 7 is a perspective view according to Modification 1-2, showing the distal end portion 14.

As shown in FIG. 7, the increased diameter portion 31Ax1 includes, at the distal end part, a narrowed portion 31Ax1*a*. The distal end opening 31Aa is formed at a distal end of the narrowed portion 31Ax1*a*. Accordingly, the inner diameter of the distal end opening 31Aa in the increased diameter portion 31Ax1 is smaller than the inner diameter of the distal end opening 31Aa in the increased diameter portion 31Ax in FIG. 6. An outer diameter of the distal end opening 31Aa is within a range of 0.9 to 2.6 mm, e.g. 1.2 mm. The inner diameter of the distal end opening 31Aa is within a range of 0.4 to 2.0 mm, e.g. 0.8 mm. According to such a configuration, the stone fragment ST may be prevented from getting caught in the communication path 31Ac.

(Modification 1-3)

Furthermore, as Modification 1-3, a projection direction of normal saline that is fed from the opening 31*b* may be made an obliquely forward direction.

Figure 8:
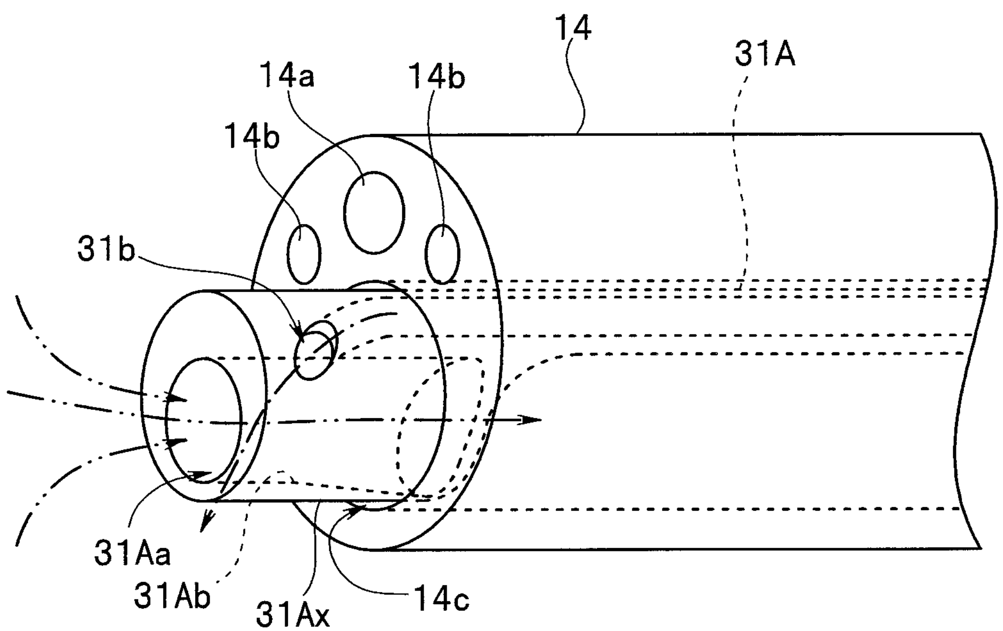
FIG. 8 is a perspective view according to Modification 1-3 of the first embodiment, showing the distal end portion of the insertion section.

FIG. 8 is a perspective view according to Modification 1-3, showing the distal end portion 14.

As shown in FIG. 8, a distal end part of a lumen in the liquid feeding tube 31A is formed inside the increased diameter portion 31Ax in a manner bent, on a distal end side, relative to the center axis of the liquid feeding tube 31A. In other words, a flow path of normal saline that communicates with the opening 31*b* in the liquid feeding tube 31A is formed bent along an outer circumferential surface of the increased diameter portion 31Ax. Accordingly, as indicated by a dash-dotted line, normal saline is fed in a direction that is at a predetermined angle relative to a plane including the center axis of the liquid feeding tube 31A and the opening 31*b*.

According to such a configuration, normal saline can be perfused inside the kidney along an inner wall of the kidney, and the stone fragment ST can be suctioned up inside the kidney and be efficiently collected.

(Modification 1-4)

Furthermore, as Modification 1-4, a cross-sectional shape of the treatment instrument insertion conduit 11*a* may be shaped to have a recess 11*a*1. The recess 11*a*1 is formed as a groove in a longitudinal axis direction of the treatment instrument insertion conduit 11*a*. The liquid feeding tube 31 can be inserted along the recess 11*a*1.

Figure 9:
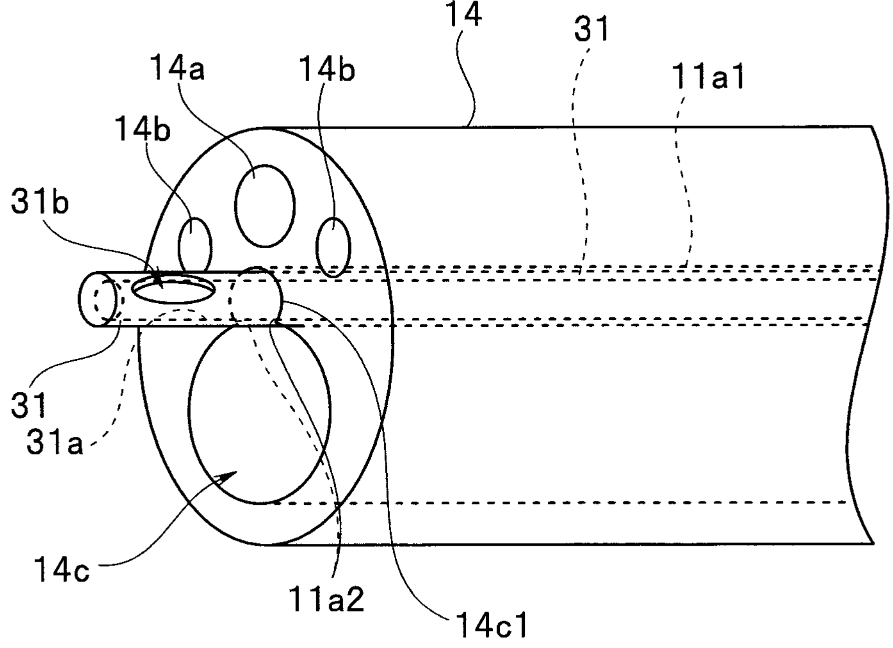
FIG. 9 is a perspective view according to Modification 1-4 of the first embodiment, showing the distal end portion of the insertion section.

FIG. 9 is a perspective view according to Modification 1-4, showing the distal end portion 14.

As shown in FIG. 9, the treatment instrument insertion conduit 11*a* includes the recess 11*a*1 on an inner circumferential surface. The recess 11*a*1 is formed along a longitudinal axis of the treatment instrument insertion conduit 11*a*. A cross-sectional shape of the treatment instrument insertion conduit 11*a* orthogonal to the longitudinal axis is a shape where two circles are partially overlapped. The recess 11*a*1 is formed in a circle with a smaller diameter between the two circles.

The liquid feeding tube 31 can be inserted in the recess 11*a*1, and two wall portions 11*a*2 are formed such that the liquid feeding tube 31 does not move from the recess 11*a*1 to the treatment instrument insertion conduit 11*a*. The two wall portions 11*a*2 are formed along the treatment instrument insertion conduit 11*a*.

Accordingly, the shape of the opening 14*c* in the distal end portion 14 is a shape where two circles or two ovals are partially overlapped, and the wall portions 11*a*2 are intersecting parts of the two circles or the two ovals.

According to Modification 1-4, the stone fragment ST can more easily pass through the treatment instrument insertion conduit 11*a*.

(Modification 1-5)

Furthermore, as Modification 1-5, a tube that is extendable and contractible or a tube, a cross-sectional shape of which can be easily deformed, may be used as the liquid feeding tube to be inserted in the treatment instrument insertion conduit 11*a*.

Figure 10:
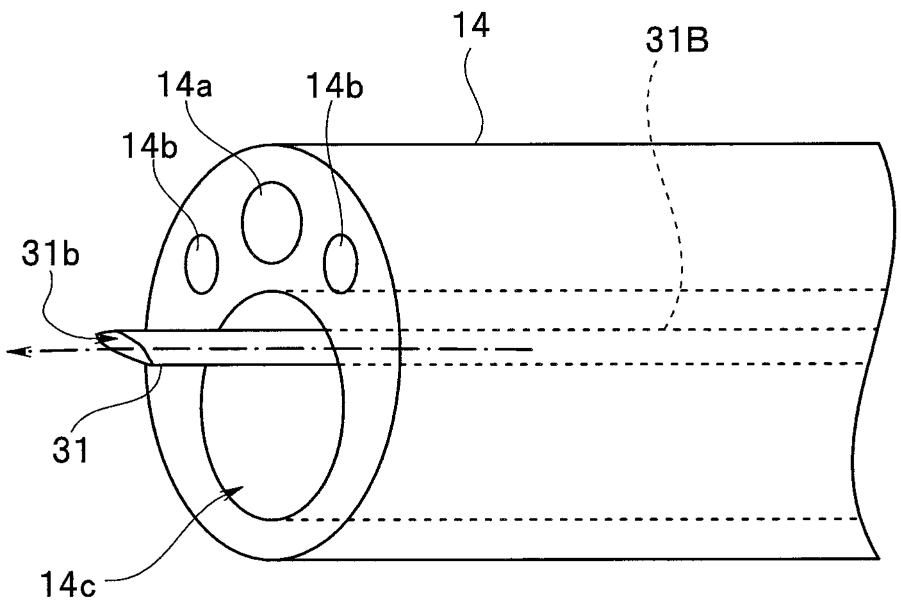
FIG. 10 is a perspective view according to Modification 1-5 of the first embodiment, showing the distal end portion of the insertion section.

FIG. 10 is a perspective view according to Modification 1-5, showing the distal end portion 14.

A liquid feeding tube 31B is made from an extremely thin member, and a cross-sectional shape orthogonal to a center axis of the liquid feeding tube 31B is deformable. A material of the liquid feeding tube 31B is polyethylene, for example. The liquid feeding tube 31B is formed from a material that is extendable and contractible or that can be easily deformed. A thickness of the liquid feeding tube 31B is 0.1 mm or less, e.g. 0.02 mm.

The liquid feeding tube 31B is extendable and contractible or the cross-sectional shape of the liquid feeding tube 31B is very easily deformed, and when the liquid feeding pump 41 is driven, normal saline can be fed from the opening 31*b* at the distal end.

Because the liquid feeding tube 31B is made from an extremely thin member, an organ inside the subject is hardly damaged even when the liquid feeding tube 31B comes into contact with the organ.

Moreover, because the liquid feeding tube 31B is made from an extremely thin member, bending capability of the bending portion 15 of the insertion section 11 is hardly reduced.

When the stone fragment ST hits an outer side of the liquid feeding tube 31B, a shape of the liquid feeding tube 31B is easily deformed, and the suctioned stone fragment ST is not easily caught in the liquid feeding tube, and the stone fragment ST can be easily collected.

Furthermore, when the stone fragment ST gets caught in the treatment instrument insertion conduit 11*a*, if liquid feeding is temporarily stopped, the liquid feeding tube 31B deforms and shrinks, and the stone fragment ST that is caught may be released and the stone fragment ST may possibly be collected.

Note that the liquid feeding tube 31B itself does not have rigidity, and insertion into the treatment instrument insertion conduit 11*a* is performed using a guide wire or the like, or by obtaining a certain level of rigidity by liquid feeding.

As described above, according to the first embodiment and each modification described above, there can be provided a perfusion device that is capable of achieving both functions of liquid suction and liquid feeding so as to enable collection of a stone fragment of a relatively large size.

Second Embodiment

In the first embodiment, the treatment instrument insertion conduit 11*a* is used for liquid suction, and a tube inserted in the treatment instrument insertion conduit 11*a* is used as the liquid feeding tube, but in the present embodiment, the treatment instrument insertion conduit 11*a* is used for liquid feeding, and a tube inserted in the treatment instrument insertion conduit 11*a* is used as a liquid suction tube.

(Configuration)

A configuration of a perfusion system according to the second embodiment is substantially the same as the configuration of the perfusion system 1 according to the first embodiment. Accordingly, description of components which is the same as the components of the perfusion system 1 according to the first embodiment will be omitted by using the same reference signs and numbers, and different components will be described.

Figure 11:
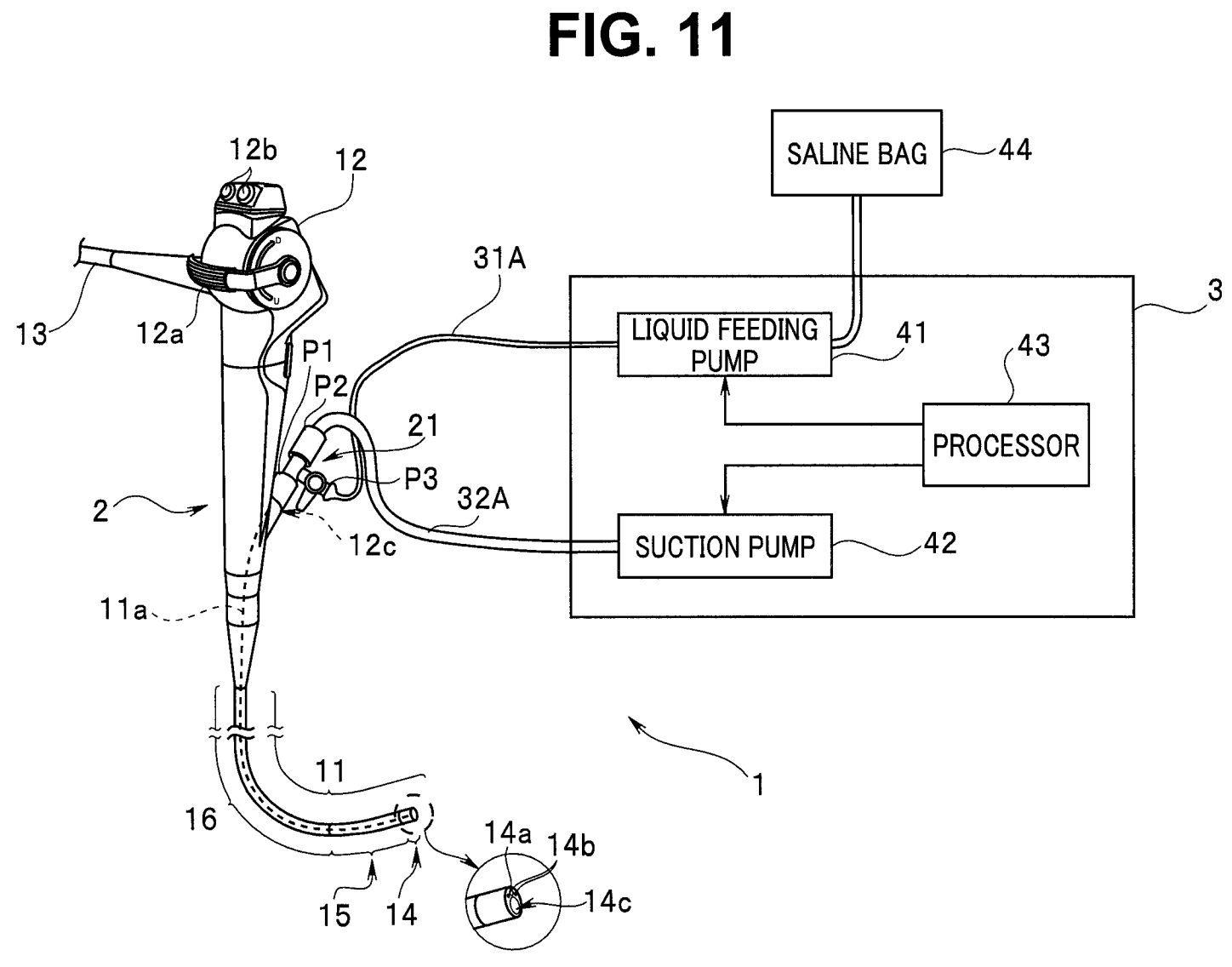

FIG. 11 is a configuration diagram according to the second embodiment, showing the perfusion system 1 including the endoscope 2 and the liquid feeding/suction device 3. As shown in FIG. 11, in the present embodiment, a liquid suction tube 32A is inserted in the port P2 of the T-shaped tube 21, and the liquid feeding tube 31A is connected to the port P3. The liquid suction tube 32A has such a length that allows a distal end of the liquid suction tube 32A to protrude from the opening 14*c* in the distal end portion 14 of the insertion section 11, as described later.

Figure 12:
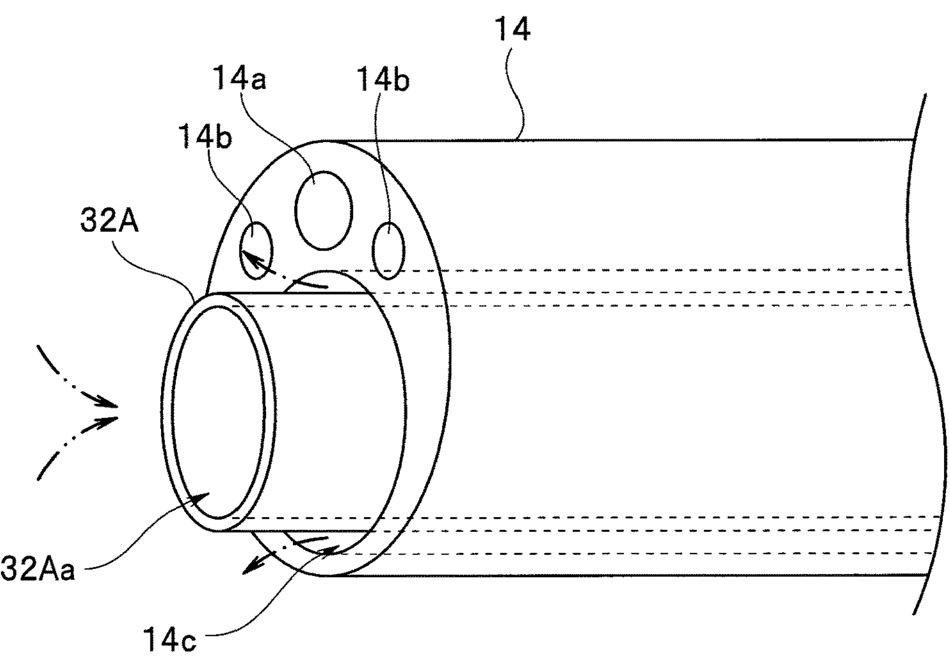
FIG. 12 is a perspective view according to the second embodiment, showing a distal end portion of an insertion section.

FIG. 12 is a perspective view according to the present embodiment, showing the distal end portion 14. FIG. 12 shows a state where the liquid suction tube 32A is inserted, via the T-shaped tube 21, in the treatment instrument insertion conduit 11*a* from the port P2 of the T-shaped tube 21, and the distal end of the liquid suction tube 32A protrudes from the opening 14*c* in the distal end portion 14 of the endoscope 2.

As shown in FIG. 12, an outer diameter of the liquid suction tube 32A is smaller than the inner diameter of the opening 14*c* in the distal end portion 14 (that is, the inner diameter of the treatment instrument insertion conduit 11*a*). In other words, the liquid suction tube 32A is configured to be insertable in the treatment instrument insertion conduit 11*a*, and includes an opening 32Aa at a distal end part.

The inner diameter of the treatment instrument insertion conduit 11*a* is within a range of 1.0 to 2.6 mm, e.g. 1.8 mm. The outer diameter of the liquid suction tube 32A is within a range of 0.4 to 2.4 mm, e.g. 1.6 mm, and an inner diameter of the liquid suction tube 32A is within a range of 0.3 to 2.2 mm, e.g. 1.4 mm.

(Operation)

As in the first embodiment, a surgeon inserts a laser probe (not shown) configured to emit laser light for breaking a kidney stone from the second port P2 of the T-shaped tube 21, and breaks the stone while the surgeon looks at the endoscopic image.

When the stone is broken into stone fragments of a predetermined size or smaller, the laser probe is removed from the second port P2 of the T-shaped tube 21.

Then, the surgeon attaches a distal end portion of the liquid feeding tube 31A to the third port P3 of the T-shaped tube 21. The surgeon inserts the distal end part of the liquid suction tube 32A from the second port P2 of the T-shaped tube 21.

The surgeon checks, looking at the endoscopic image, that the distal end part of the liquid suction tube 32A is in a state of protruding from the opening 14*c* in the distal end portion 14, and then, rotates the second fixing ring 53 in the predetermined direction around the center axis O to fix the liquid suction tube 32A.

Then, the surgeon causes the liquid feeding/suction device 3 to operate, and simultaneously performs feeding and suction of liquid. By also taking into account an amount of liquid discharge outside the endoscope, the processor 43 drives the liquid feeding pump 41 and the suction pump 42 in such a way that a good balance is achieved between an amount of liquid feeding and an amount of liquid suction.

As indicated by dash-dotted lines in FIG. 12, due to liquid feeding, normal saline is fed through a gap between the inner circumferential surface of the treatment instrument insertion conduit 11*a* and an outer circumferential surface of the liquid suction tube 32A. As indicated by dash-dot-dotted lines, normal saline is suctioned from the distal end opening 32Aa of the liquid suction tube 32A.

In other words, in a state where the distal end opening 32Aa protrudes from the distal end of the treatment instrument insertion conduit 11*a*, suction of normal saline is performed from the distal end opening 32Aa of the liquid suction tube 32A, and feeding of normal saline is performed through the gap between the outer circumferential surface of the liquid suction tube 32A and the inner circumferential surface of the treatment instrument insertion conduit 11*a*. When normal saline is suctioned, the stone fragment ST is also suctioned and drawn into the liquid suction tube 32A. The stone fragment ST can pass through the liquid suction tube 32A.

Because two tubes, namely, the liquid feeding tube 31 and the liquid suction tube 32, are not provided in parallel inside the insertion section 11, and only the liquid suction tube 32A is inserted in the treatment instrument insertion conduit 11*a*, the inner diameter of the treatment instrument insertion conduit 11*a* can be increased within a possible range. The outer diameter of the liquid suction tube 32A can be increased within a range where a predetermined amount of liquid feeding can be secured.

Accordingly, because a relatively large stone fragment can be collected, a stone collecting treatment time can be reduced, and burden on the patient can be reduced.

Furthermore, in the present embodiment, when a stone fragment gets caught in the liquid suction tube 32A, the stone fragment can be collected when the surgeon pulls out the liquid suction tube 32A, and then, collection of the stone fragment can be continued by replacing the liquid suction tube 32A.

Furthermore, in the present embodiment, the stone fragment passes through the liquid suction tube 32A, and thus, the inner circumferential surface of the treatment instrument insertion conduit 11*a* is not damaged by the stone fragment.

(Modification 2-1)

Note that, as Modification 2-1, the distal end part of the liquid suction tube 32A can be narrowed to make the inner diameter of the liquid suction tube 32A even smaller.

Figure 13:
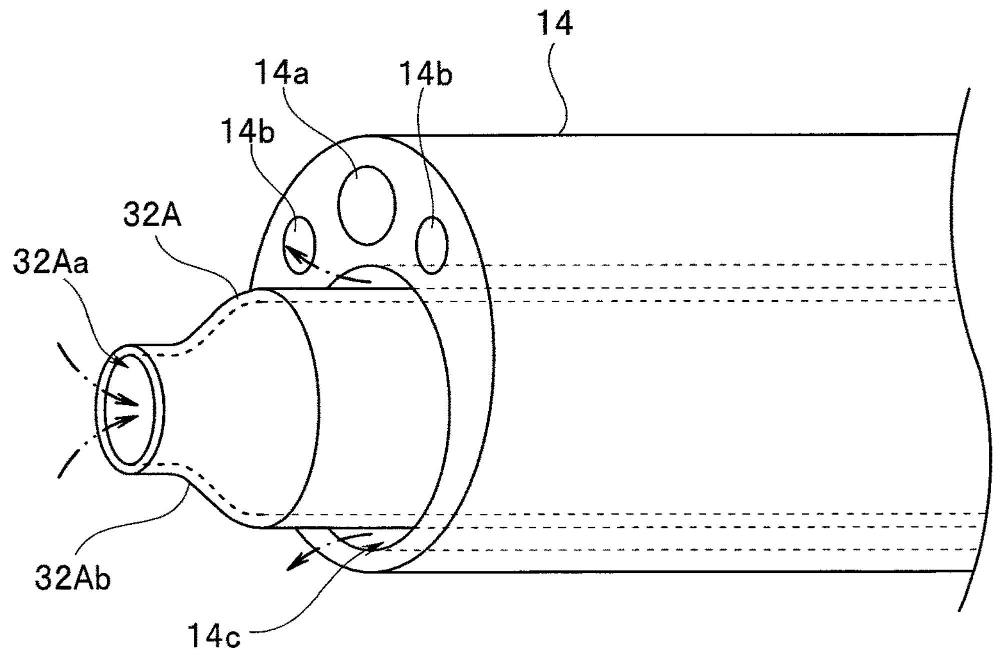
FIG. 13 is a perspective view according to Modification 2-1 of the second embodiment, showing the distal end portion of the insertion section.

FIG. 13 is a perspective view according to Modification 2-1, showing the distal end portion 14. FIG. 13 shows a state where the distal end of the liquid suction tube 32A protrudes from the opening 14*c* in the distal end portion 14 of the endoscope 2.

As shown in FIG. 13, the liquid suction tube 32A includes, at the distal end part, a narrowed portion 32Ab. The narrowed portion 32Ab is formed such that an inner diameter is reduced toward a distal end. A distal end opening 32Aa is formed at the distal end of the narrowed portion 32Ab. Accordingly, an inner diameter of the distal end opening 32Aa of the narrowed portion 32Ab is smaller than an inner diameter of the distal end opening 32Aa of the liquid suction tube 32A in FIG. 12. An outer diameter of the distal end opening 32Aa is within a range of 0.4 to 2.4 mm, e.g. 1.3 mm. The inner diameter of the distal end opening 32Aa is within a range of 0.2 to 2.1 mm, e.g. 1.1 mm.

Also in Modification 2-1, suction of normal saline is performed from the distal end opening 32Aa, and feeding of normal saline is performed through the gap between the outer circumferential surface of the liquid suction tube 32A and the treatment instrument insertion conduit 11*a*. According to such a configuration, the stone fragment ST can be prevented from getting caught in the liquid suction tube 32A.

As described above, according to the embodiment and the modification described above, there can be provided a perfusion device that is capable of achieving both functions of liquid suction and liquid feeding so as to enable collection of a stone fragment of a relatively large size.

Third Embodiment

In the first and second embodiments described above, liquid feeding and liquid suction are each performed using one tube or one channel, but in the present embodiment, one more tube is provided on an outer circumferential part of the insertion section, and one of liquid feeding and liquid suction is enabled to be also performed through the one channel.

(Configuration)

A configuration of a perfusion system according to the third embodiment is substantially the same as the configuration of the perfusion system 1 according to the first embodiment. Accordingly, description of components which is the same as the components of the perfusion system 1 according to the first embodiment will be omitted by using the same reference signs and numbers, and different components will be described.

Figure 14:
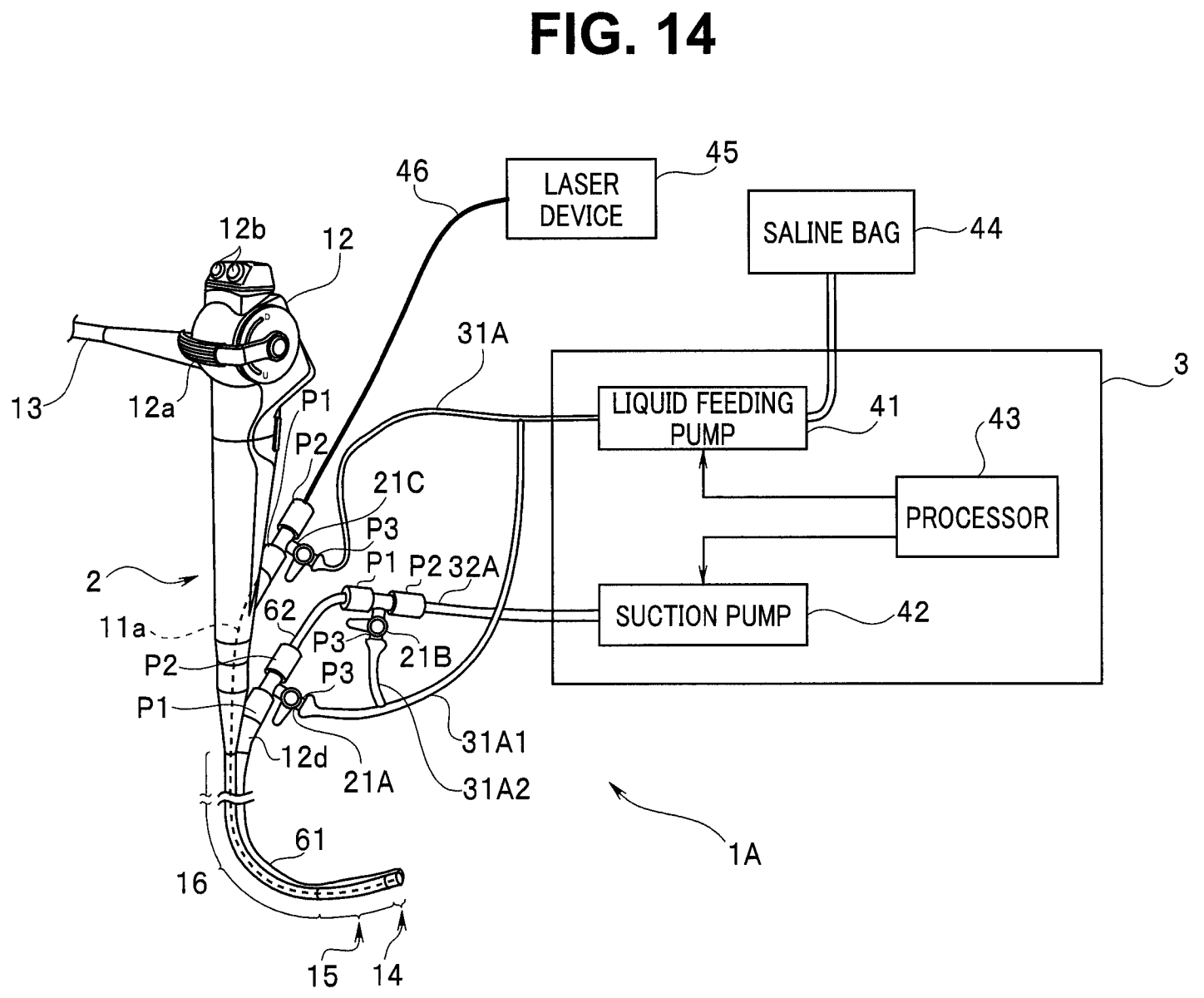

FIG. 14 is a configuration diagram according to the third embodiment, showing a perfusion system 1A including the endoscope 2 and the liquid feeding/suction device 3. FIG. 14 also shows a laser device 45. A laser probe 46 extends from the laser device 45. The laser probe 46 has a diameter that allows insertion from a T-shaped tube 21C attached to the treatment instrument insertion opening 12*c* of the endoscope 2 into the treatment instrument insertion conduit 11*a*.

The laser device 45 includes a light source, and laser light from the light source enters a proximal end surface of the laser probe 46, and is emitted from a distal end surface of the laser probe 46.

A fixing member 12*d* for fixing a proximal end of a tube 61 is provided at the distal end portion of the operation section 12. The fixing member 12*d* may be fixed to the operation section 12 by a screw, an adhesive, or the like. The port P2 of a T-shaped tube 21A and the proximal end of the tube 61 are connected and fixed to the fixing member 12*d*. The T-shaped tube 21A according to the present embodiment has a same configuration as the T-shaped tube 21 shown in FIG. 2. The T-shaped tube 21C described later also has a same configuration as the T-shaped tube 21 shown in FIG. 2.

A T-shaped tube 21B described later is a member that, like the T-shaped tube 21A, includes the cock 55, and that controls a direction of flow of liquid that flows into the T-shaped tube 21B. The cock 55 is rotatable around the center axis 55*a*. For example, with the T-shaped tube 21B, when the cock 55 is at the position shown in FIG. 2, the first port P1 and the second port P2 communicate with each other, and the third port P3 does not communicate with the first port P1 or the second port P2. Furthermore, with the T-shaped tube 21B, when the cock 55 is rotated by 90 degrees around the center axis 55*a* from the position shown in FIG. 2, the first port P1 and the third port P3 communicate with each other, but the second port P2 does not communicate with the first port P1 or the third port P3.

The fixing member 12*d* includes an internal conduit (not shown), and the port P1 of the T-shaped tube 21A is connected to one end of the internal conduit, and the proximal end of the tube 61 is connected to the other end of the internal conduit.

The tube 61 is a tube made of the same material as the liquid feeding tube 31B described in Modification 1-5 of the first embodiment, and is an extendable and contractible tube or a tube, the cross-sectional shape of which is deformable. Accordingly, the insertion section 11 includes, on an outer side, the tube 61 that includes a conduit 61*a* (FIG. 15) where liquid passes. The tube 61 includes an opening 61*b* (FIG. 15) at a distal end. Like the insertion section 11, the tube 61 is an insertion appliance that is configured to be insertable inside a subject.

The port P1 of the T-shaped tube 21A is connected to the fixing member 12*d*.

A tube 62 is inserted from the port P2 of the T-shaped tube 21A, and the tube 62 can be inserted into the tube 61 through the T-shaped tube 21A. Moreover, the tube 62 is configured to be insertable into the tube 61, and the tube 62 includes an opening 62*a* at a distal end part. An outer diameter of the tube 62 is within a range of 0.8 to 2.4 mm, e.g. 1.8 mm.

A distal end of a branched liquid feeding tube 31A1 branched from the liquid feeding tube 31A is connected to the port P3 of the T-shaped tube 21A.

Figure 15:
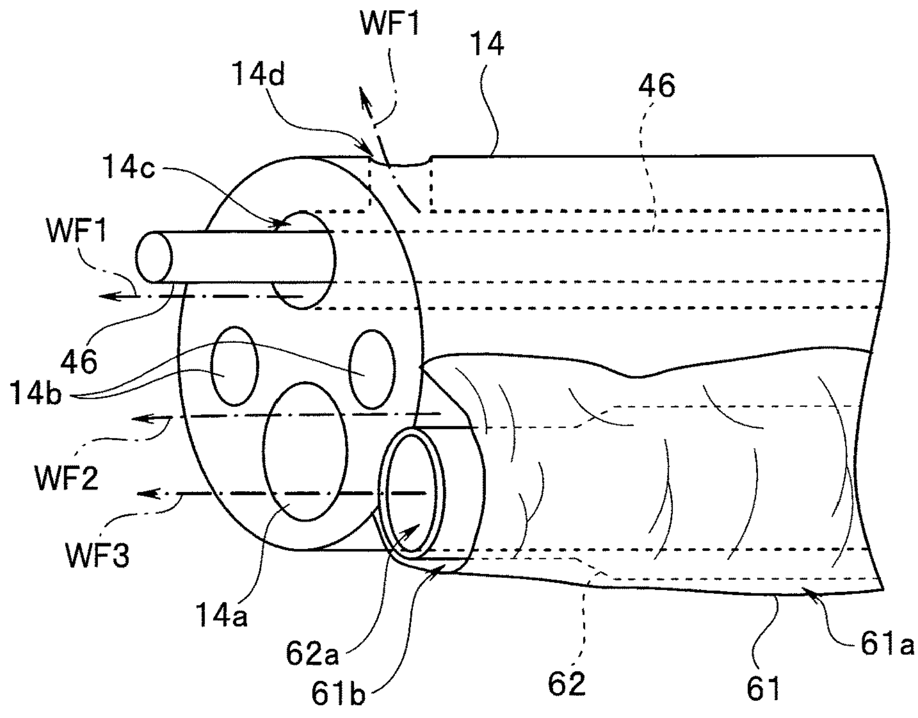
FIG. 15 is a perspective view according to the third embodiment, showing a distal end portion of an insertion section.
Figure 16:
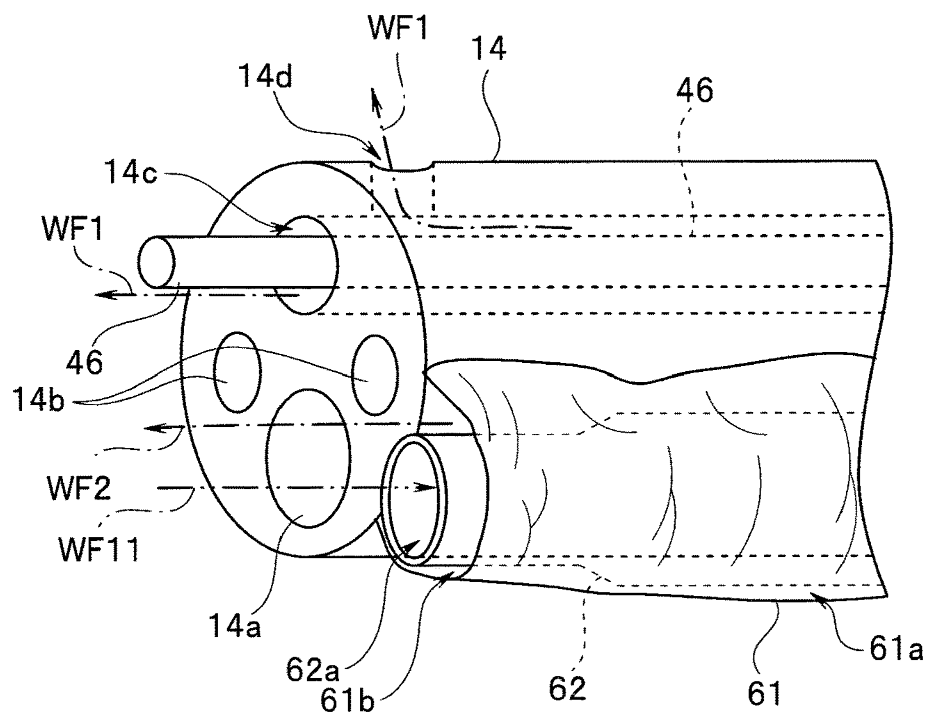
FIG. 16 is a perspective view according to the third embodiment, showing the distal end portion of the insertion section.

FIGS. 15 and 16 are perspective views of the distal end portion 14, where the tube 61 is provided along the insertion section 11.

The tube 61 is fixed to an outer surface of the insertion section 11 by an adhesive or the like along the longitudinal axis of the insertion section 11. In other words, the tube 61 is an external conduit that is provided outside the insertion section 11, and that is made of a material that is extendable and contractible or deformable. The tube 61 is made from an extremely thin member which is the same as described in Modification 1-5 of the first embodiment described above, and a cross-sectional shape orthogonal to a center axis of the tube 61 is deformable. A material of the tube 61 is polyethylene, for example. Accordingly, the tube 61 is very easily deformed.

The tube 62 is inserted inside the tube 61. The tube 62 has flexibility, and is made of rubber or PTFE, for example.

A distal end of the tube 62 inserted from the port P2 of the T-shaped tube 21A is inserted in a manner capable of protruding from a distal end opening of the tube 61.

Referring back to FIG. 14, a proximal end of the tube 62 is connected to the port P1 of the T-shaped tube 21B.

The distal end of the liquid suction tube 32A is connected to the port P2 of the T-shaped tube 21B. One end of a branched liquid feeding tube 31A2 branched from the branched liquid feeding tube 31A1 is connected to the port P3 of the T-shaped tube 21B.

The port P1 of the T-shaped tube 21C is connected to the treatment instrument insertion opening 12*c*.

The laser probe 46 is inserted from the port P2 of the T-shaped tube 21C to pass through the treatment instrument insertion conduit 11*a* so as to be able to protrude from the opening 14*c* in the distal end portion 14. The inner diameter of the opening 14*c* in the present embodiment is within a range of 0.3 to 2.0 mm, e.g. 1.2 mm.

The distal end of the liquid feeding tube 31A is connected to the port P3 of the T-shaped tube 21C.

As shown in FIG. 15, in the present embodiment, a distal end of the laser probe 46 can protrude or retract from the opening 14*c*. The treatment instrument insertion conduit 11*a* is used for liquid feeding. Accordingly, an opening 14*d* that communicates with the treatment instrument insertion conduit 11*a* is provided in a side surface of the distal end portion 14.

As indicated by dash-dotted lines, normal saline that is fed is fed through a gap between an outer circumferential surface of the laser probe 46 and the opening 14*c* and from the opening 14*d*.

(Operation)

According to the configuration described above, a route of flow of liquid inside the T-shaped tube 21B can be changed by operating the cock 55 (FIG. 2) of the T-shaped tube 21B.

During stone dusting by the laser probe 46, the cock 55 is operated such that the ports P1 and P3 of the T-shaped tube 21B communicate with each other. The liquid feeding pump 41 is driven, and the suction pump 42 is stopped.

As a result, as shown in FIG. 15, with respect to normal saline from the liquid feeding pump 41, a flow WF1 out of the opening 14*c*, a flow WF2 out through a gap between an inner wall of the tube 61 and an outer circumferential surface of the tube 62, and a flow WF3 out of the distal end opening 62*a* of the tube 62 are generated at the distal end portion 14 during laser stone dusting.

The flow WF1 is a flow of normal saline that flowed into the port P3 of the T-shaped tube 21C. The flow WF2 is a flow of normal saline that flowed into the port P3 of the T-shaped tube 21A. The flow WF3 is a flow of normal saline that flowed into the port P3 of the T-shaped tube 21B. Due to the flow WF3, the amount of perfusion is increased during stone dusting, and an increase in temperature of normal saline in the kidney can be suppressed.

During collection of the stone fragment ST after stone dusting, the cock 55 is operated such that the ports P1 and P2 of the T-shaped tube 21B communicate with each other. The liquid feeding pump 41 and the suction pump 42 are driven.

As a result, as shown in FIG. 16, with respect to normal saline from the liquid feeding pump 41, the flow WF1 out of the opening 14*c*, and the flow WF2 out through the gap between the inner wall of the tube 61 and the outer circumferential surface of the tube 62 are generated at the distal end portion 14 during collection of the stone fragment ST. Furthermore, a flow WF11 of suction from the distal end opening 62*a* of the tube 62 is generated at the distal end portion 14.

The flow WF1 is a flow of normal saline that flowed into the port P3 of the T-shaped tube 21C. The flow WF2 is a flow of normal saline that flowed into the port P3 of the T-shaped tube 21A. The flow WF11 is a flow of normal saline suctioned by the port P2 of the T-shaped tube 21B. Accordingly, the T-shaped tube 21B configures a switch configured to switch between feeding and suction of normal saline by the tube 62.

As described above, in a state where the distal end opening 62*a* of the tube 62 protrudes from the distal end of the tube 61, one of feeding and suction of normal saline is performed through the distal end opening 62*a* of the tube 62, and feeding of liquid is performed through a gap between the outer circumferential surface of the tube 62 and an inner circumferential surface of the tube 61.

Therefore, according to the present embodiment, by switching a route of the normal saline between stone dusting and collection, an increase in temperature in the kidney can be suppressed during stone dusting by increasing the amount of perfusion, and efficiency of collection of the stone fragment ST can be increased by using the wider tube 62 at the time of collection.

As described above, according to each embodiment and each modification described above, there can be provided a perfusion device and a perfusion method that are capable of achieving both functions of liquid suction and liquid feeding so as to enable collection of a stone fragment of a relatively large size.

Note that, as indicated by a dash-dot-dotted line in FIG. 1, in each embodiment and each modification described above, a proximal end part of the liquid feeding tube 31 may have a greater diameter than a part that is inserted in the treatment instrument insertion conduit 11*a*. More specifically, in a state where the liquid feeding tube 31 is inserted in the treatment instrument insertion conduit 11*a* and protrudes from the opening 14*c* in the distal end portion 14, an inner diameter of the proximal end part of the liquid feeding tube 31 between the port P2 of the T-shaped tube 21 and the liquid feeding pump 41 can be greater than an inner diameter of the part of the liquid feeding tube 31 inserted in the treatment instrument insertion conduit 11*a* such that conduit resistance of the liquid feeding tube 31 is reduced. Accordingly, the conduit resistance of the liquid feeding tube 31 can be reduced, and the perfusion system can be configured by the liquid feeding pump 41 that is small and inexpensive and that has small output.

Furthermore, each embodiment and each modification described above give a description citing an endoscope including treatment instrument insertion channel as an example, but each embodiment and each modification can also be applied to a catheter including a conduit or an access sheath configured to guide a treatment instrument. For example, the conduit of the catheter or a conduit of the access sheath may be used as a liquid feeding or suction channel, and a tube inserted in the conduit of the catheter, or the conduit of the access sheath may be used for suction or liquid feeding.

The present invention is not limited to the embodiments described above, and various changes, modifications, and the like can be made within the gist of the present invention.

What is claimed is:

1. A perfusion device, comprising:

an insertion appliance configured to be insertable inside a subject, the insertion appliance including a conduit disposed along a longitudinal axis; and a tube configured to be insertable in the conduit, the tube including;

a main part, an opening at a distal end part having a larger diameter than the main part, a first flow path formed in the tube, and a second flow path formed in the tube, wherein:

the distal end part includes a first opening at a side surface and a second opening at a distal end, the first flow path penetrates both the main part and the distal end part, the first flow path including a main path portion extending along a longitudinal axis, the second flow path penetrates only the distal end part along a longitudinal axis and communicates with the second opening, and in a state where the distal end part protrudes from a distal end of the conduit, one of feeding and suction of liquid is allowed to be performed through the first opening of the tube, and another of feeding and suction of the liquid is allowed to be performed through the second opening of the tube.

2. The perfusion device according to claim 1, wherein the first flow path includes a bent portion inclined from the main path portion toward a distal side and an outer circumferential side to communicate with the first opening, and in the state where the distal end part protrudes from the distal end of the conduit, the another of feeding and suction of the liquid is allowed to be performed through both the second opening and a gap between an outer circumferential surface of the tube and an inner circumferential surface of the conduit.

3. The perfusion device according to claim 2, wherein the distal end part includes a narrowed portion that is formed in such a way that an outer diameter is reduced toward the distal end of the tube, suction of the liquid is performed through both the second opening and the gap, and feeding of the liquid is performed through the gap between the first opening.

4. The perfusion device according to claim 1, wherein an inner diameter of the second flow path is narrower toward the second opening of the distal end part.

5. The perfusion device according to claim 1, wherein a cross-sectional shape of the conduit orthogonal to the longitudinal axis is a shape where two circles are partially overlapped, and the tube is inserted in one of the two circles.

6. The perfusion device according to claim 1, wherein the tube further includes a proximal end part having a greater inner diameter than the main part that is inserted in the insertion appliance.

7. A perfusion method, comprising:

inserting a tube into a conduit of an insertion appliance configured to be inserted into a subject, the tube including a main part, a distal end part having a larger diameter than the main part, a first flow path formed in the tube, and a second flow path formed in the tube, the distal end part including a first opening at a side surface and a second opening at a distal end, the first flow path penetrating both the main part and the distal end part, the first flow path including a main path portion extending along a longitudinal axis, and the second flow path penetrating only the distal end part along the longitudinal axis and communicating with the second opening;

causing the distal end part of the tube to protrude from a distal end of the conduit;

performing one of feeding and suction of liquid from the first opening; and performing another of feeding and suction of the liquid through the second opening.

8. The perfusion method according to claim 7, wherein the first flow path includes a bent portion inclined from the main path portion toward a distal side and an outer circumferential side to communicate with the first opening, and performing the another of feeding and suction of the liquid including performing the another of feeding and suction of the liquid through both the second opening and a gap between an outer circumferential surface of the tube and an inner circumferential surface of the conduit.

9. The perfusion method according to claim 8, wherein the distal end part includes a narrowed portion that is formed in such a way that an outer diameter is reduced toward the distal end of the tube, suction of the liquid is performed through both the second opening and the gap, and feeding of the liquid is performed through the gap between the outer circumferential surface of the tube and the inner circumferential surface of the conduit.

10. The perfusion method according to claim 7, wherein an inner diameter of the second flow path is narrower toward the second opening of the distal end part.

11. The perfusion method according to claim 7, wherein a cross-sectional shape of the conduit orthogonal to a longitudinal axis is a shape where two circles are partially overlapped, and the tube is inserted in one of the two circles.

12. The perfusion method according to claim 7, wherein the tube further includes a proximal end part having a greater inner diameter than the main part that is inserted in the insertion appliance.

13. A perfusion system, comprising:

an insertion appliance configured to be insertable inside a subject, the insertion appliance including a conduit disposed along a longitudinal axis;

a tube configured to be insertable in the conduit, the tube including:

a main part, a distal end part having a larger diameter than the main part, a first flow path formed in the tube, and a second flow path formed in the tube;

a liquid supply source configured to supply liquid to the tube; and a fluid control device configured to control a supply flow rate of the liquid by the liquid supply source, wherein:

the distal end part includes a first opening at a side surface and a second opening at a distal end, the first flow path penetrates both the main part and the distal end part, the first flow path including a main path portion extending along the longitudinal axis, the second flow path penetrates only the distal end part along the longitudinal axis and communicates with the second opening, and in a state where the distal end part protrudes from a distal end of the conduit, one of feeding and suction of liquid is allowed to be performed through the first opening of the tube, and another of feeding and suction of the liquid is allowed to be performed through the second opening.

14. The perfusion system according to claim 13, wherein the first flow path includes a bent portion inclined from the main path portion toward a distal side and an outer circumferential side to communicate with the first opening, and in the state where the distal end part protrudes from the distal end of the conduit, the another of feeding and suction of the liquid is allowed to be performed through both the second opening and a gap between an outer circumferential surface of the tube and an inner circumferential surface of the conduit.

15. The perfusion system according to claim 14, wherein an inner diameter of the second flow path is narrower toward the second opening of the distal end part.

16. The perfusion system according to claim 15, wherein a cross-sectional shape of the conduit orthogonal to the longitudinal axis is a shape where two circles are partially overlapped, and the tube is inserted in one of the two circles.

17. The perfusion system according to claim 13, wherein the distal end part includes a narrowed portion that is formed in such a way that an outer diameter is reduced toward the distal end of the tube, suction of the liquid is performed through both the second opening and the gap, and feeding of the liquid is performed through the first opening.

18. A perfusion device, comprising:

an insertion appliance including:

an insertion section configured to be insertable inside a subject, the insertion section including a conduit disposed along a longitudinal axis, an operation section including a switch configured to switch between feeding and suction of liquid, and an external conduit which is provided outside the insertion section, the external conduit being made of a material that is extendable and contractible or that is deformable; and a tube configured to be insertable in the external conduit, the tube including an opening at a distal end part, wherein, in a state where the opening protrudes from a distal end of the external conduit, one of feeding and suction of the liquid is allowed to be performed through the opening of the tube in a manner switchable by the switch, and another of feeding and suction of the liquid is allowed to be performed through a gap between an outer circumferential surface of the tube and an inner circumferential surface of the external conduit.

* * * * *